United States Patent
Bai et al.

(10) Patent No.: US 10,464,061 B2
(45) Date of Patent: *Nov. 5, 2019

(54) NANOCHANNEL DEVICE WITH THREE DIMENSIONAL GRADIENT BY SINGLE STEP ETCHING FOR MOLECULAR DETECTION

(71) Applicant: International Business Machines Corporation, Armonk, NY (US)

(72) Inventors: Jingwei Bai, Los Angeles, CA (US); Qinghuang Lin, Yorktown Heights, NY (US); Gustavo A. Stolovitzky, Riverdale, NY (US); Chao Wang, Ossining, NY (US); Deqiang Wang, Ossining, NY (US)

(73) Assignee: INTERNATIONAL BUSINESS MACHINES CORPORTAION, Armonk, NY (US)

( * ) Notice: Subject to any disclaimer, the term of this patent is extended or adjusted under 35 U.S.C. 154(b) by 192 days.

This patent is subject to a terminal disclaimer.

(21) Appl. No.: 15/096,933

(22) Filed: Apr. 12, 2016

(65) Prior Publication Data
US 2016/0220996 A1 Aug. 4, 2016

Related U.S. Application Data

(63) Continuation of application No. 14/199,248, filed on Mar. 6, 2014, now Pat. No. 9,322,061.

(51) Int. Cl.
B81C 1/00 (2006.01)
B01L 3/00 (2006.01)
(Continued)

(52) U.S. Cl.
CPC ... *B01L 3/502707* (2013.01); *B01L 3/502761* (2013.01); *B81C 1/00103* (2013.01);
(Continued)

(58) Field of Classification Search
CPC ........... H01L 21/266; H01L 21/823885; H01L 27/14616
See application file for complete search history.

(56) References Cited

U.S. PATENT DOCUMENTS 6,685,841 B2  2/2004 Lopez et al.
6,696,022 B1  2/2004 Chan et al.
(Continued)

OTHER PUBLICATIONS

A. Meller, et al., "Voltage-Driven DNA Translocation Through a Nanopore," The American Physical Society; vol. 86, No. 15, Physical Review Letters, Apr. 9, 2001; pp. 3435-3438.
(Continued)

*Primary Examiner* — Mohammad M Choudhry
(74) *Attorney, Agent, or Firm* — Cantor Colburn LLP

(57) ABSTRACT

A technique includes forming a gradient channel with width and depth gradients. A mask is disposed on top of a substrate. The mask is patterned with at least one elongated channel pattern having different elongated channel pattern widths. A channel is etched in the substrate in a single etching step, the channel having a width gradient and a corresponding depth gradient both simultaneously etched in the single etching step according to the different elongated channel pattern widths in the mask.

20 Claims, 12 Drawing Sheets

(51) Int. Cl.
*C12Q 1/6869* (2018.01)
*G01N 33/487* (2006.01)
*C12Q 1/6874* (2018.01)
*B82Y 40/00* (2011.01)

(52) U.S. Cl.
CPC ......... *C12Q 1/6869* (2013.01); *C12Q 1/6874* (2013.01); *G01N 33/48721* (2013.01); *B01L 2200/0663* (2013.01); *B01L 2200/12* (2013.01); *B01L 2300/0816* (2013.01); *B01L 2300/0861* (2013.01); *B01L 2300/0896* (2013.01); *B01L 2300/12* (2013.01); *B01L 2400/0415* (2013.01); *B01L 2400/086* (2013.01); *B81B 2201/058* (2013.01); *B81B 2203/0338* (2013.01); *B81B 2203/0392* (2013.01); *B82Y 40/00* (2013.01)

(56) References Cited

U.S. PATENT DOCUMENTS

| | | | |
|---|---|---|---|
| 7,217,562 | B2 | 5/2007 | Cao et al. |
| 8,137,569 | B2 | 3/2012 | Harnack et al. |
| 8,138,068 | B2 | 3/2012 | Li et al. |
| 8,142,708 | B2 | 3/2012 | Schwartz et al. |
| 9,322,061 | B2 * | 4/2016 | Bai .................. C12Q 1/6869 |
| 9,733,185 | B2 * | 8/2017 | Cao .................. G01N 21/6486 |
| 2012/0021204 | A1 | 1/2012 | Pei et al. |
| 2015/0076555 | A1 | 3/2015 | Yang et al. |

OTHER PUBLICATIONS

C. Dekker, "Solid-State Nanopores," Nature Nanotechnology; vol. 2; Apr. 2007; Nature Publishing Group; pp. 209-215.

D. Branton, et al., "The Potential and Challenges of Nanopore Sequencing," Nature Biotechnology; 2008 Nature Publishing Group; vol. 26, No. 10, Oct. 2008; pp. 1146-1153.

G. Ando, et al., "Directly Observing the Motion of DNA Molecules Near Solid-State Nanopores," ACS Nano, vol. 6, No. 11, 2012, pp. 10090-10097.

H. Cao, et al., "Fabrication of 10 nm Enclosed Nanofluidic Channels," Applied Physics Letters; vol. 81, No. 1; Jul. 1, 2002; American Institute of Physics; pp. 174-176.

H. Cao, et al., "Gradient Nanostructures for Interfacing Microfluidics and Nanofluidics," Applied Physics Letters, vol. 81, No. 16, 2002, pp. 3058-3060.

J. Fu, et al., "A Patterned Anisotropic Nanofluidic Sieving Structure for Continuous-Flow Separation of DNA and Proteins," Nature Nanotechnology; vol. 2; Feb. 2007; 2007 Nature Publishing Group; pp. 121-128.

J. Han, et al., "Entropic Trapping and Escape of Long DNA Molecules at Submicron Size Constriction," Phys. Rev. Lett., vol. 83, 1999, pp. 1688-1691.

J. O. Tegenfeldt, et al., "The Dynamic of Genomic-Length DNA Molecules in 100-nm Channels," PNAS; Jul. 27, 2004; vol. 101; No. 30; pp. 10979-10983.

M. Firnkes, et al., "Electrically Facilitated Translocations of Proteins Through Silicon Nitride Nanopores: Conjoint and Competitive Action of Diffusion, Electrophoresis, and Electroosmosis," 2010 American Chemical Society; Nano Lett. 2010, 10 pp. 216-222.

MEMS Clearinghouse, "Fabricating MEMS and Nanotechnology," internet retrieval: http://www.memsnet.org/about/fabrication.html pp. 1-9; Mar. 7, 2014.

W. Reisner, et al., "Statics and Dynamics of Single DNA Molecules Confined in Nanochannels," PRL 94, 196101 (2005) Physical Review Letters, May 20, 2005; The American Physical Society; pp. 196101-1-196101-4.

* cited by examiner

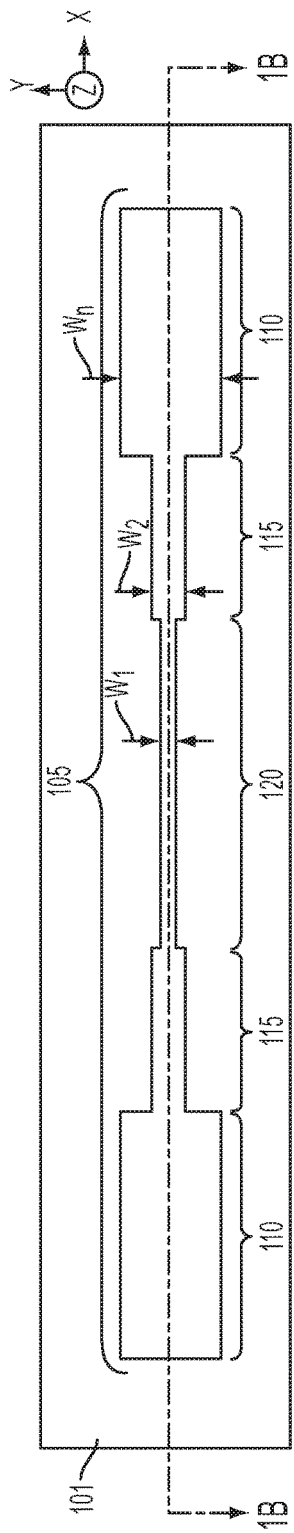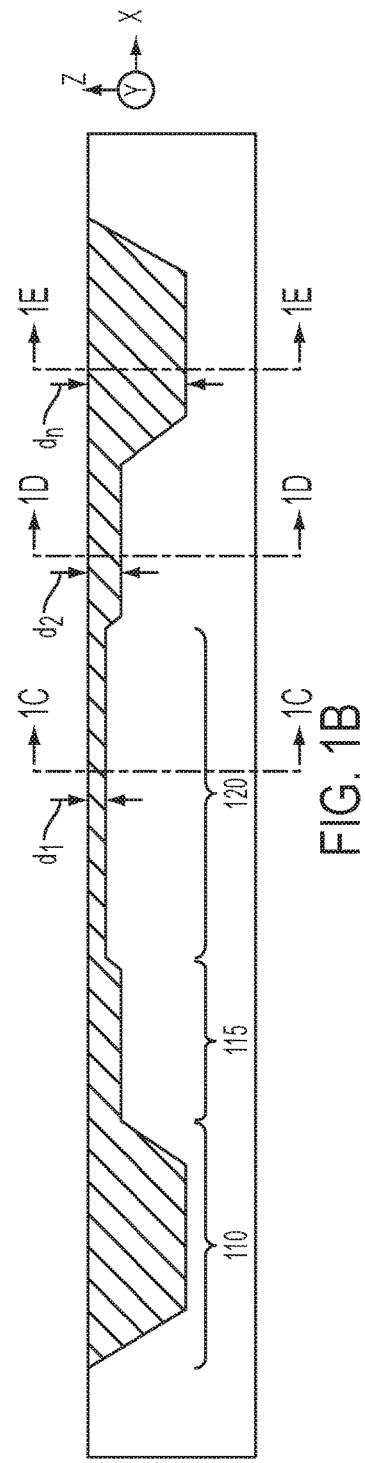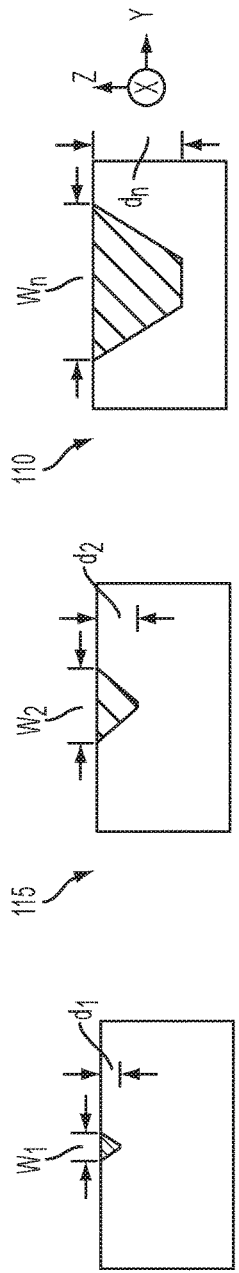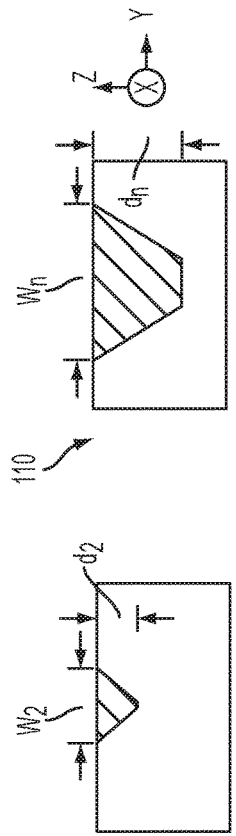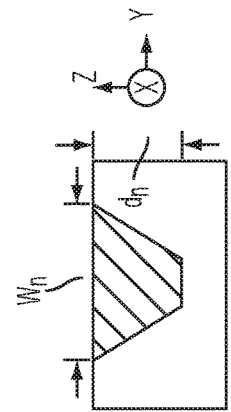

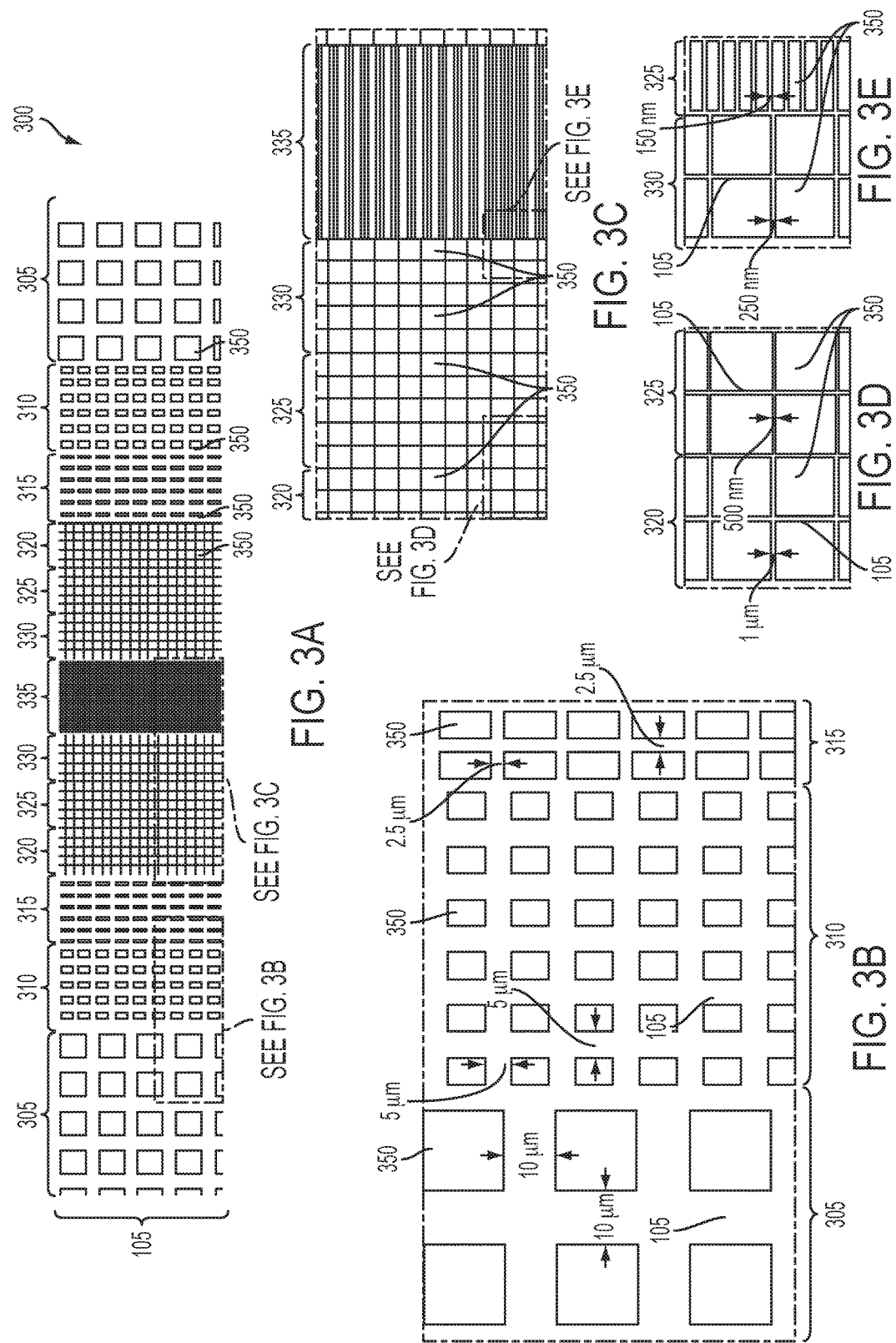

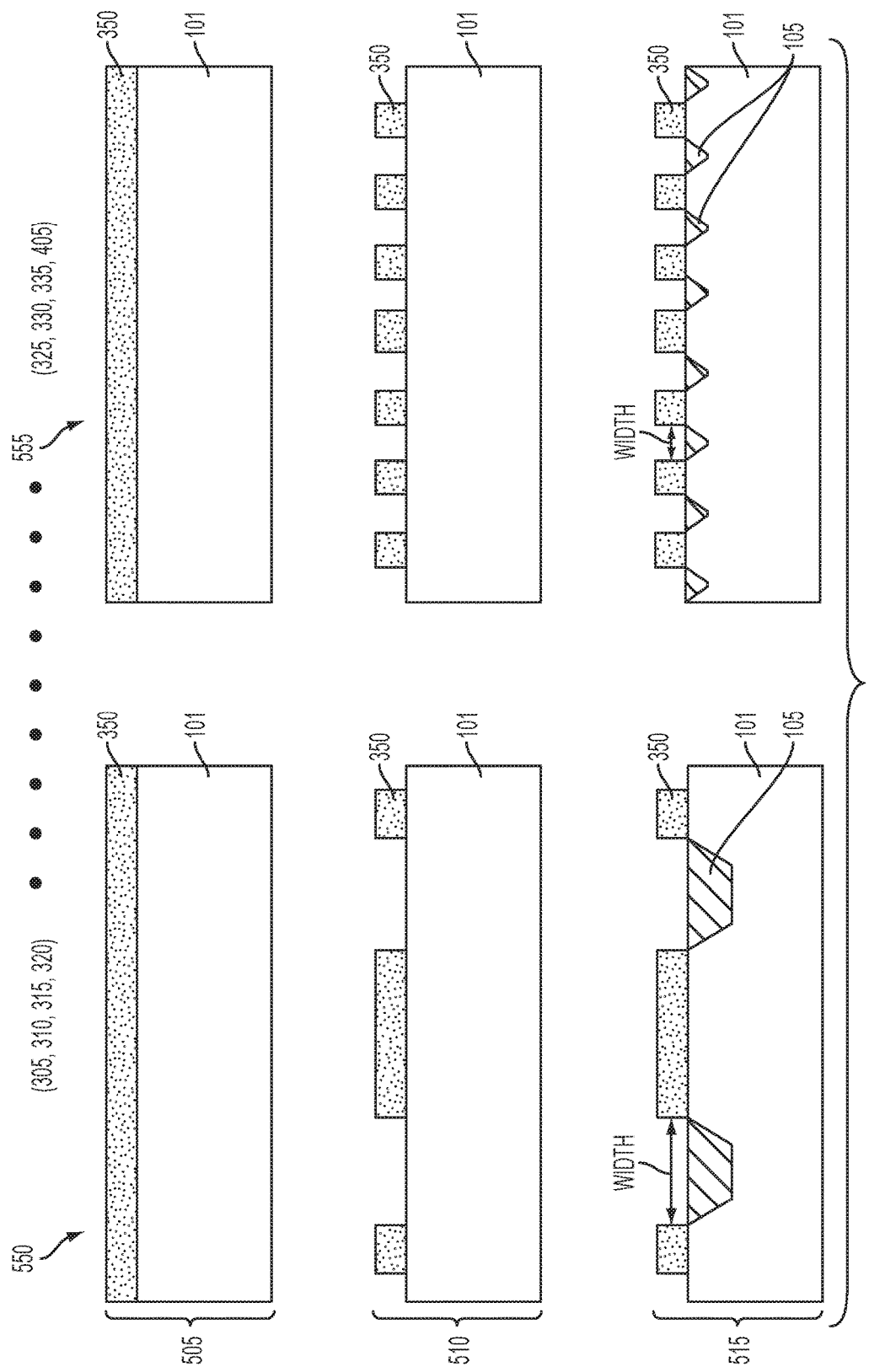

NANOCHANNEL DEVICE WITH THREE DIMENSIONAL GRADIENT BY SINGLE STEP ETCHING FOR MOLECULAR DETECTION

DOMESTIC PRIORITY

This application is a continuation of and claims priority from U.S. patent application Ser. No. 14/199,248, filed on Mar. 6, 2014, entitled "NANOCHANNEL DEVICE WITH three DIMENSIONAL GRADIENT BY SINGLE STEP ETCHING FOR MOLECULAR detection", the entire contents of which are incorporated herein by reference.

BACKGROUND

Embodiments relate to nanodevices, and more particularly to channels in nanodevices with depth gradient and width gradient.

Nanopore sequencing is a method for determining the order in which nucleotides occur on a strand of deoxyribonucleic acid (DNA). A nanopore is a small hole in the order of several nanometers in internal diameter. The theory behind nanopore sequencing relates to what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be placed around the nanopore so that DNA bases can be differentiated while the DNA passes through the nanopore.

SUMMARY

According to an embodiment, a method of forming a gradient channel with width and depth gradients is provided. The method includes disposing a mask on top of a substrate, where the mask is patterned with at least one elongated channel pattern having different elongated channel pattern widths. A channel is etched in the substrate in a single etching step, in which the channel has a width gradient and a corresponding depth gradient both simultaneously etched in the single etching step according to the different elongated channel pattern widths in the mask.

According to an embodiment, a method of forming gradient channels with width and depth gradients is provided. The method includes disposing a mask on top of a substrate, where the mask is patterned with an array of elongated channel patterns having different elongated channel pattern widths. An array of channels is etched in the substrate in a single etching step. The array of channels each has a width gradient and a corresponding depth gradient both simultaneously etched in the single etching step according to the different elongated channel pattern widths in the mask.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

FIGS. 1A, 1B, 1C, 1D, and 1E illustrate a channel with various widths and depths at different portions according to an embodiment.

FIGS. 3A, 3B, 3C, 3D, and 3E illustrate a biochip with channel arrays according to an embodiment, in which:

FIG. 3A illustrates the biochip with various channel arrays of channels of different widths and depths.

FIG. 3B is an enlarged view of one section of the biochip.

FIG. 3C is an enlarged view of another section of the biochip.

FIG. 3D is an enlarged view of one section in FIG. 3C.

FIG. 3E is an enlarged view of another other section in FIG. 3C.

FIGS. 5A and 5B together illustrate fabrication operations to form channels with various depths based on their respective width at any particular region of the channels according to an embodiment.

DETAILED DESCRIPTION

Figure 2A:
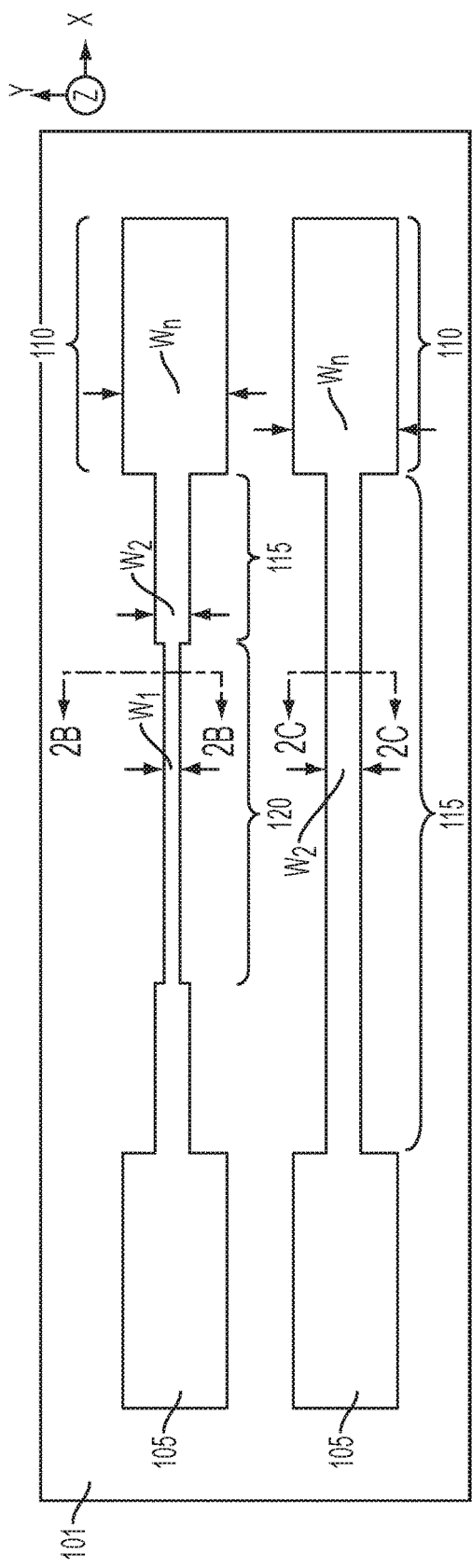
FIGS. 2A, 2B, and 2C illustrate a channel array with various widths and depths at different portions according to an embodiment.

Accurate and inexpensive sensing of biopolymers, especially nucleic acids (DNA, RNA), is critical to the understanding of many scientific and biomedical applications. A high-throughput and robust device to electrically sequence the biopolymers is important. Solid-state bio-sensing techniques, such as artificial nanopores and channels, have been integrated into fluidics for sensing of many types of biopolymer molecules, including DNA, RNA, proteins, etc.

One particular issue remaining for sensing biopolymers is a large entropic barrier for biopolymers to transport from a large dimension into a small dimension, for example the channel width or depth. The barrier height greatly lowers the translocation rate of the biopolymers, causes very long clogging events, and can cause configurationally instabilities of the biopolymers. All the above can lead to reduced capture rates of the target molecules and thus severely affect the detection.

Embodiments utilize anisotropic silicon (Si) etching to create gradient microchannel and nanochannel depth from gradient channel widths. This method simplifies fabrication and controls the nanochannel dimensions (both width and depth) down to sub 5 nm by combining Si oxidation and/or conformal dielectric deposition.

Embodiments provide a method of fabricating nanofluidic channels with gradient channel depths by first patterning a hard mask with various channel dimensions (which may include microchannel widths and nanochannel widths) and then anisotropic Si wet etching the substrate. Due to the highly anisotropic and selective properties of Si wet etching (KOH, TMAH), the channel depths can be controlled so that:

(1) etching is minimal in the regions where the channel dimensions are small (in the nanoscale and/or nanochannel regions), and the vertical depths are dependent on and largely determined by lateral (nanochannel) dimensions (i.e., widths) but insensitive to the etching time;

(2) the etching depth in the regions where the lateral channel dimensions are larger (microscale and/or microchannel regions) is determined by the etching time.

Through a single step wet etching, shallow channels are formed in nanoscale regions with the depths controlled by the lateral dimensions (i.e., widths); while at the same time, deep channels (in the microchannel regions) are created for fast feeding fluid. Such fluidic channels with different depths are optimal for high-throughput sorting and sensing biomolecules, such as proteins, DNA, RNA, cells, etc. The gradient depth is also favorable for gradually linearizing the biopolymers and increasing the capturing rate. To further reduce the channel dimensions, conformal dielectric coating and/or Si oxidation can be used. Finally, the fluidic channels can be sealed by wafer bonding or sacrificial sealing.

Note that a fluidic channel device is the same as a fluidic channel chip or a biochip.

FIGS. 1A, 1B, 1C, 1D, and 1E (generally referred to as FIG. 1) illustrate schematics showing a channel with various widths and depths (i.e., width gradient and depth gradient) at different portions according to embodiments. FIG. 1A is a top view (X-Y plane view) showing a channel 105 with (three) different widths of w1, w2, wn.

The different widths of the channel 105 individually correspond to and define different depths as shown in FIGS. 1B through 1E. The area having the (smallest) width w1 is designated as a channel region 120 in the channel 105, the area having the (middle) width w2 is designated as channel region 115, and the area having the (largest) width wn is designated as channel region 110.

The channel 105 is formed in a substrate 101 by wet (anisotropic) etching in a single etching step. The substrate may be a silicon substrate. For example, a mask is deposited on the substrate 101 and patterned in the shape/pattern of the channel 105. In other words, the various widths (i.e., width gradient) are patterned in the mask. The wet etching solution is applied to the substrate 101 to etch the channel 105 in the substrate 101 according to the pattern in the mask, and the mask is removed.

FIG. 1B is the cross-sectional view (X-Z plane view) of the channel 105 (along the dash line A-A in FIG. 2A) to show the different channel depths d1, d2, dn respectively corresponding to and determined by the different channel widths w1, w2, wn. Analogous to the regions for the different widths, the area having the (smallest/shallowest) vertical depth d1 is in the channel region 120 in the channel 105, the area having the (middle) vertical depth d2 is in the channel region 115, and the area having the (largest/deepest) vertical depth dn is in channel region 110.

FIG. 1C is the cross-sectional view (Y-Z plan view) of region 120 of the channel 105 to show that the width w1 has corresponding depth d1. FIG. 1D is the cross-sectional view (Y-Z plan view) of region 115 of the channel 105 to show that the width w2 has a corresponding depth d2. FIG. 1E is the cross-sectional view (Y-Z plan view) of region 110 of the channel 105 to show that the width wn has corresponding depth dn.

A larger width causes a larger depth, while a smaller width results in a smaller depth. For example, the width wn is larger than the width w2, and the width w2 is larger than the width w1. Correspondingly, the depth dn is larger than the depth d2, and the depth d2 is larger than the depth d1. The corresponding depth in each channel region 110, 115, and 120 is based on (and a result of) the width of the channel 105 at that particular region, and even with more and more wet etching time T, the depth of each channel region does not exceed a predetermined depth that is based on its width. The width w1, w2, wn of each channel region in channel 105 is formed by the pattern of the mask applied during wet etching in the single etching step.

Assuming the substrate 101 is a Si (100) substrate and the wet etching time T is long enough to remove the Si in the narrow regions 120 and 115 (e.g., w1 and w2 regions), then the bottom of the channel 105 is a triangular shape in those regions 120 and 115 (i.e., w1 and w2 regions) as shown in FIGS. 1C through 1E, with the formed angled sidewalls in Si (111) plane. Due to a preferred (but not a necessary) etching of Si in (100) plane and a very slow etching in (111) plane, the etching slows down dramatically (or virtually stops) on the exposed Si (111) plane. In this case, the channel depths d1, d2, do of the channel 105 are determined by their individual channel widths w1, w2, wn, which can be lithographically patterned (e.g., via a mask) within a wide range, e.g., from tens of nanometers (nm) (or single nanometers) to microns (μm). In the case of Si wet etching, the ratio of depth to width is $\eta = \tan(54.7°) = 0.707$. This causes the vertical depth to be a predetermined/predefined maximum value based on the width of the channel during the single etching step of anisotropic wet etching.

If the etching time is long enough, the region 110 can have a triangle bottom just as regions 115 and 120. For example, when the etching time T is long enough (to reach the depth $dn = \eta \cdot wn$) during the etching of the (microchannel) region 110 with the width wn, the (microchannel) region 110 then has a triangular cross-section, and the depth is $dn = \eta \cdot wn$. Therefore, the microchannel region and nanochannel region both have a predetermined/predefined maximum vertical depth during the single etching step (with anisotropic wet etching).

If the etching time T is not long enough to reach this maximum vertical depth ($\eta \cdot wn$) for the (larger microchannel) region 110 with width wn, then the lesser vertical depth is determined by the etching rate $R_{100}$ of Si (100) plane and the etching time T, such that $dn = T \cdot R$ (in this case when the predetermined maximum vertical depth is not reached). In this way, the (microchannel) depths in region 110 can still have a flat bottom (as shown in FIG. 1E) and controlled depth, even though the narrow channel regions 115, 120 have triangular shaped bottoms (profiles).

Once the mask is deposited on the substrate 101, each of the depths d1, d2, dn (along with the respective widths w1, w2, wn) are etched in a single etching step. The single etching step is wet anisotropic etching for a predetermined etching time T. Even if the etching time T continued indefinitely (or for days), the depths d1, d2, dn are designed to stop (i.e., not increase) beyond the restriction of the respective widths w1, w2, wn (of the mask) as determined by dn=η*wn (where d1=η*w1, d2=η*w2, d3=η*w3 through dn=η*wn). By having predetermined/predefined maximum vertical depths individually based on their respective widths for the channel 105 (all etched in a single etching step for etching the channel 105), an array of channels 105 can be made in the single etching step with a depth gradient (i.e., various depths) as discussed further below according to an embodiment. That is, separate etching steps are not required to etch width w1 and depth d1, to etch width w2 and depth d2, and to etch width wn and depth dn in the channel 105 according to embodiments, as each width and its corresponding depth is simultaneously etched in the substrate 101 during the single etching step, which may take a few seconds to a few minutes depending on the designed etching depth. In contrast, conventionally creating each depth requires a full set of resist coating, lithographical patterning, etching, and surface cleaning steps, and thus multiple fabrication steps are needed to etch a channel with multiple widths and depths, and the multiple steps would typically require a much longer processing time (several days to weeks) and a much higher cost. Therefore, it can be seen that the fabrication time is greatly reduced by using the single etching step to simultaneously etch multiple channels 105 with multiple widths (as discussed in FIGS. 1-10) having corresponding multiple depths according to embodiments.

Note that FIG. 1 shows the channel 105 with three different widths and three corresponding vertical depths, but embodiments are not limited to a channel with only three different width and depth gradients. The technique applies to creating tens, twenties through hundreds of different widths and their corresponding tens, twenties through hundreds of different depths in the single etching step for multiple channels, where the channels can have the same, different, and/or a combination of the same and different width and depth gradient patterns.

Figure 2C:
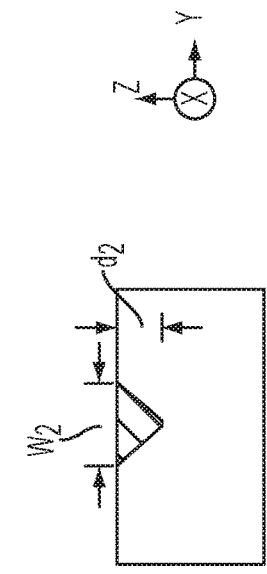
Figure 2B:
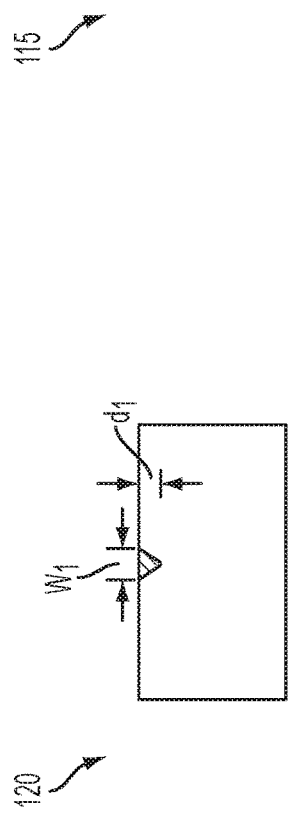

FIGS. 2A, 2B, and 2C (generally referred to as FIG. 2) illustrate patterning/etching channels 105 of different dimensions (i.e., different width and depth dimensions) at the same time (i.e., single etching step) on a wafer according to an embodiment. FIGS. 2A, 2B, and 2C illustrate a channel array (nanochannel array) showing two (or more) channels 105 with easily tunable dimensions. Using the approach of embodiments, a number (such as an array) of channels (microchannels through nanochannels) with different designed dimensions (widths and depths) can be achieved in the single etching step. FIG. 2A illustrates a top view of the channels 105 while FIGS. 2B and 2C illustrate cross-sectional views of the channels 105.

As can be seen in FIGS. 2A, 2B, and 2C, one channel 105 is etched (in the single etching step) to width w1 with corresponding depth d1 in region 120, width w2 with corresponding depth d2 in region 115, and width wn with corresponding depth dn (not shown in FIG. 2) in region 110. The other channel 105 is etched (in the same single etching step) to width w2 with corresponding depth d2 in region 115 and width wn with corresponding depth dn (not shown in FIG. 2). The parallel channels 105 in FIG. 2 are simultaneously formed with different dimensions in the single etching step.

FIGS. 3A, 3B, 3C, 3D, and 3E (generally referred to as FIG. 3) illustrate a biochip 300 with channel arrays according to an embodiment. The biochip 300 (i.e., nanodevice) incorporates the teachings of FIGS. 1 and 2. The designed microchannel and nanochannel arrays (i.e., multiple channels 105) have varied dimensions which are varied widths and depths. For example, the designed channel widths change from 10 μm to 150 nm (or even down to 10-20 nm) (i.e., from microchannels to nanochannels). The single etching step is utilized to create the different widths and their corresponding (different) vertical depths. Note that the corresponding depths (resulting from the different widths) are not shown in FIG. 3, but the depths are limited by the respective width during the single etching step as described herein. The single etching step applies for one width resulting in one depth, hundreds of different widths resulting in hundreds of different depths, and thousands of different widths resulting in thousands of different depths.

FIG. 3A illustrates the biochip 300 with the various channel arrays with channels 105 of different sizes (i.e., different widths and their corresponding depths are simultaneously etched) in channels regions 305, 310, 315, 320, 325, 330, 335. The channel regions have etched channels of different widths and depths. Seven channel regions are shown but it is understand that there can be more channel regions. A mask 350 is deposited on the substrate 101 and patterned into the various widths so that the channel regions are etched as shown in FIG. 3. The mask 350 is removed after etching in the single etching step leaving the etched array of channels 105. In one case, the mask 350 may remain and not be removed.

FIG. 3B is an enlarged view of one section of the biochip 300 to show the different channel regions 305, 310, and 315. In this example, FIG. 3B shows the channels 105 with a width (wn) of 10 μm in region 305, a width (w6) of 5 μm in region 310, and a width (w5) of 2.5 μm in region 315. The channel regions 305, 310, and 315 may be considered the microchannel region because the channels 105 all have channel widths (lateral dimensions) in the micrometer range (i.e., at least 1 μm).

FIG. 3C is an enlarged view of another section of the biochip 300 to show the different channel regions 320, 325, 330, and 335. From two sections in FIG. 3C, FIG. 3D is an enlarged view of one section and FIG. 3E is an enlarged view of the other section in FIG. 3C.

In FIG. 3D, region 320 has channels 105 with a width (w4) of 1 μm, and region 325 has channels 105 with a width (w3) of 500 nm. Accordingly, region 320 is in the microchannel region because region 320 has a channel width (lateral dimension) of at least 1 micrometer/micron.

In FIG. 3E, region 330 has channels 105 with a width (w2) of 250 nm, and region 335 has channels 105 with a width of 150 nm. Regions 325, 330, and 335 are considered in the nanochannel region because they each have a channel width of less than 1 micrometer.

In FIG. 3, exemplary channel widths continuously decrease in lateral size from width wn through w1, and correspondingly, their individual vertical depths continuously decrease in vertical depth from depth dn through d1 (all channels 105 with the depth gradient are etched simultaneously during the single etching step), where width wn has depth dn all the way through width w1 with depth d1. In this example, there are seven different channel widths, where width wn is the largest width 10 μm (in region 305) through w1 as the smallest width 150 nm (in region 335); the remaining regions 310, 315, 320, 325, 335 constitute the different channel widths in between. Similarly, there are seven different vertical depths (not shown), where depth dn is the largest depth and depth d1 is the smallest depth. For example, the smallest channel depth according the design would be approximately 100 nm from a 150 nm width. The largest depth is in the microchannel region, depending on the etching rate and time, and the largest depth can range from approximately 500 nm to tens of micrometers.

Figure 4:
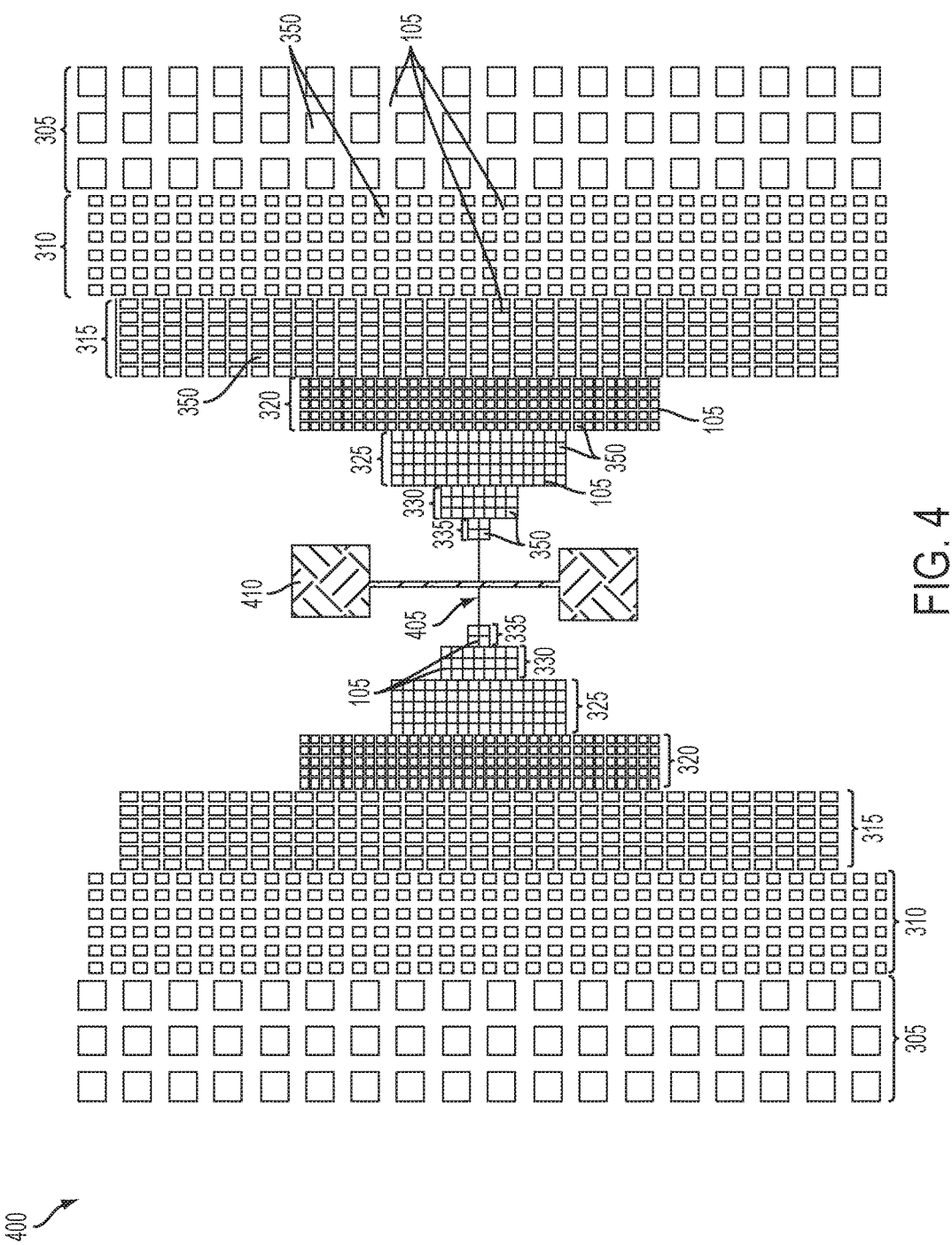
FIG. 4 is a biochip that narrows to a single nanochannel passage according to an embodiment.

FIG. 4 is a biochip 400 that narrows to a single nanochannel passage 405 according to an embodiment. The biochip 400 is a nanodevice that incorporates the teachings of FIGS. 1-3.

In FIG. 4, the designed single nanochannel 405 is connected to varied channel dimensions as discussed above in FIG. 3. As the only passage for biomolecules, the single nanochannel 405 makes it possible to align an electronic detector 410 across the single nanochannel 405 for electronic detections.

As discussed in FIG. 3, FIG. 4 shows the different (i.e., different widths and corresponding different depths) channel regions 305, 310, 315, 320, 325, 330, 335 (e.g., from largest channel width to smallest) of the channels 105. The width of the single nanochannel 405 can be the same width as or smaller width than the width of the channels 105 in region 335.

Note that the mask 350 in FIGS. 3 and 4 may be removed from the top of the substrate 101 after the single etching step that simultaneously etches the channels 105 (and channel 405) with different widths and depths. The vertical depth for each channel width is not explicitly shown in FIGS. 3 and 4 but it is understood that each vertical depth of the channel is directly based on and determined by its channel width in each particular region of the channels 105, as has been discussed herein.

Figure 5B:
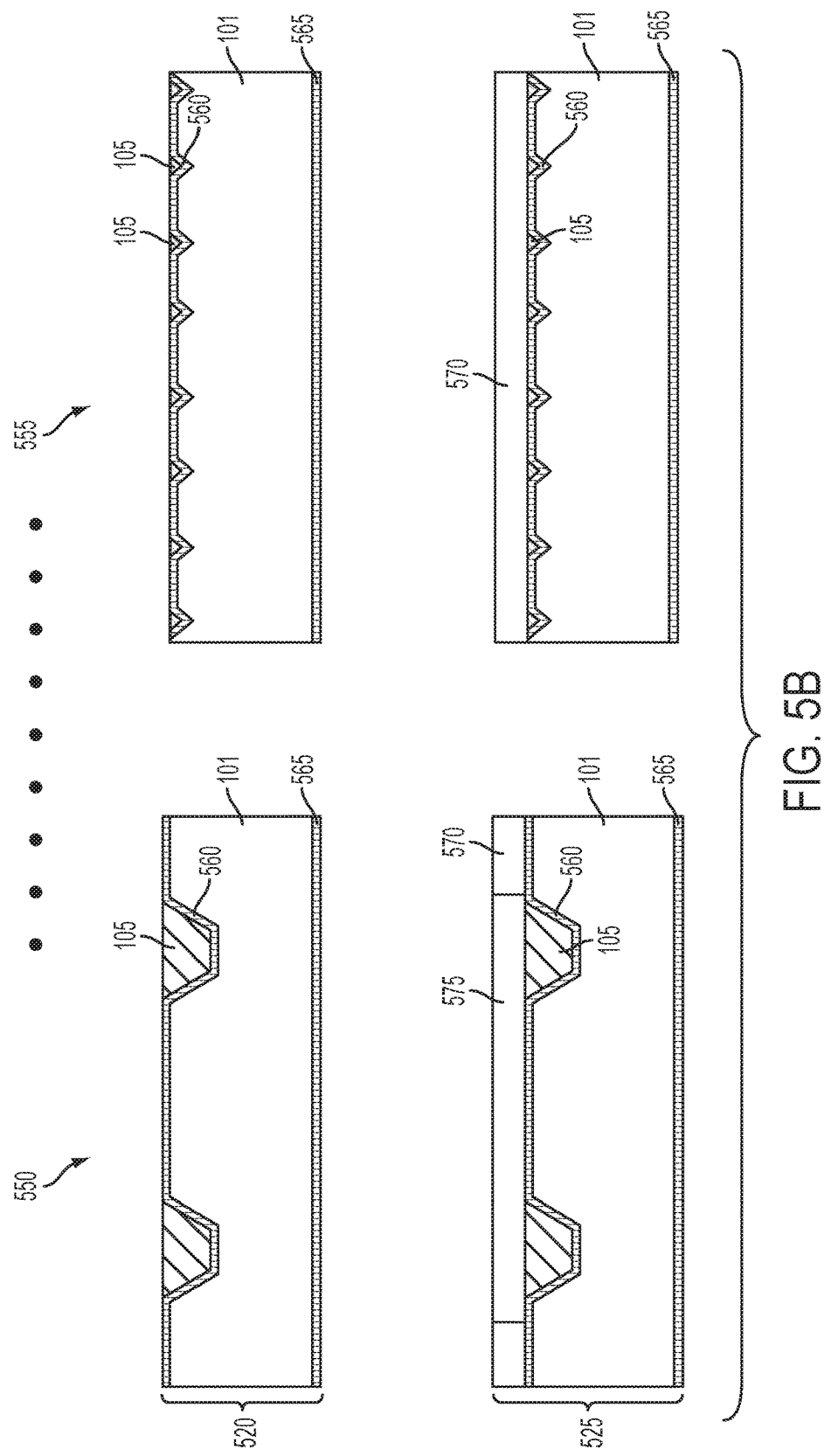

FIGS. 5A and 5B (generally referred to as FIG. 5) illustrate fabrication operations for (Si) etching to form channels 105 with various depths based on their respective width at any particular region of the channels 105 according to an embodiment. Note that FIG. 5 only shows example fabrication of two general views 550 and 555, but analogously applies to all of the different regions 305, 310, 315, 320, 325, 330, 335, and 405. View 550 describes fabricating (in the single etching step) any and/or all of the microchannel regions discussed herein that have a width (lateral dimension) of at least 1 μm, while view 555 describes simultaneously (in the single etching step) fabricating any and/or all of the nanochannels regions that have a width (lateral dimension) less than 1 μm.

FIG. 5 illustrates the process to fabricate the devices (300, 400) in FIGS. 1-4 and 6-10. The fabrication starts with a Si (100) substrate. Other materials can also be utilized, such as Ge, GaAs, sapphire, etc.

At block 505, a thin mask layer 350 is deposited on the substrate 101. The mask layer 350 may be made of a thin $SiO_2$ layer that is deposited on the Si substrate 101. For example, the substrate 101 has a thin layer of the hard mask 350 on top, which can be silicon oxide, silicon nitride, or other dielectric materials that can effectively mask Si wet etching. The thickness of this hard mask 350 depends on the etching resistance of the hard mask material itself. For $SiO_2$, the hard mask layer 350 can be either thermally grown oxide or deposited oxide by chemical vapor deposition (CVD). The particular thickness of $SiO_2$ is 20 nm to 50 nm, but can be from 5 nm to hundreds of nanometers (too thin may not be enough as a mask, and too thick film requires longer time to strip after Si etching).

At block 510, the hard mask layer 350 is patterned according to the desired widths for the channel regions 305, 310, 315, 320, 325, 330, 335, 405. The $SiO_2$ mask layer 350 is patterned in the microchannel through nanochannel regions for masking the Si substrate 101 during etching. The mask layer 350 is patterned to have different patterned widths such as the widths w1-wn (eventually resulting in the corresponding depths d1-dn).

For example, the $SiO_2$ hard mask is patterned by lithography tools (photolithography, electron beam lithography, etc.) and reactive ion etching (RIE) in microchannel and nanochannel regions. The patterned Si wafer with the hard mask 350 on top should be first briefly dipped in etchant to clear possible residual hard mask in the patterned opening windows (otherwise a thin hard mask in the window can significantly block etching in the subsequent single etching step). The etchant for clearing any $SiO_2$ in the elongated pattern (used for making the channels 105) can be diluted hydrofluoric acid solution. Clearing debris from the elongated pattern in the hard mask 350 is not defined as the single etching step that etches the channels 105, as understood by one skilled in the art.

At block 515, anisotropic wet etching of the (Si) substrate 101 is performed in the single etching step to form deep microchannels, shallow nanochannels, and interface channels (not shown) between the vertical depths of the microchannels and nanochannels, as described in FIGS. 1-4 and 6-8. This single etching step simultaneously forms the (array of) channels 105 with the widths w1-wn and corresponding depths d1-dn (in the channel regions 305, 310, 315, 320, 325, 330, 335, 405) in the substrate 101 without multiple etching steps.

The depths of the different channels 105 depend on the etching rate (which depends on the etching conditions, such as etchant type, concentration, temperature, etc.), etching time, and channel widths. The etchant for Si etching is commonly TMAH (Tetramethylammonium hydroxide), but other chemicals such as KOH (potassium hydroxide), NaOH (sodium hydroxide), etc., are also possible. This ends the single etching step utilized to form the channels 105 with both a width gradient and depth gradient, which can be different in each channel 105 as desired.

At block 520, the ($SiO_2$) hard mask layer 350 is stripped away by wet etching (e.g., by hydrofluoric acid). Stripping away the hard mask layer 350 is not defined as the single etching step that etches the channels 105, and block 520 simply removes the hard mask 350 as understood by one skilled in the art. Additionally as an option, the Si (substrate 101) can be oxidized to form a top and bottom oxidation layer 560 and 565 of uniform and flat $SiO_2$, or other insulating materials can be deposited onto the Si substrate.

At block 525, the formed device with channels 105 can be bonded to a coverglass 570 to seal the channels 105. An opening 575 can be in the coverglass 570 over the largest region (with the widest channel 105) so that molecules (i.e., biopolymers) can be added into the channel 105.

For example, the patterned wafer can be optionally diced, thoroughly cleaned, bonded to a coverglass, and annealed (e.g., at 300° C.-600° C.) to seal the channels. The coverglass can be made in borosilicate to best match the thermal expansion coefficient of that of Si. The cleaning process can be performed by rinsing with solvents (acetone and isopropanol, etc.), soaking in Piranha solution (mixture of sulfuric acid and hydrogen peroxide), deionized water rinsing, and drying. The Piranha solution can be replaced by others such as RCA1 (mixture of ammonium hydroxide and hydrogen peroxide) or RCA2 (mixture of chloric acid and hydrogen peroxide). The coverglass can be pre-drilled with access holes, and aligned to the reservoir regions of the channels for sample manipulation. The coverglass may have different thicknesses, e.g., a thickness of 170 μm for the best (but not a necessity) imaging resolution using fluorescence microscope.

The fabrication process may occur on a wafer (a large piece, non-diced material), a chip (diced individual device), and/or a substrate (the supporting materials for a wafer/chip). The fabrication of the device utilizes standard CMOS-compatible microscale and nanoscale patterning techniques, which enable large-scale and low-cost integration and provide repeatable and uniform critical dimension control.

Figure 6:
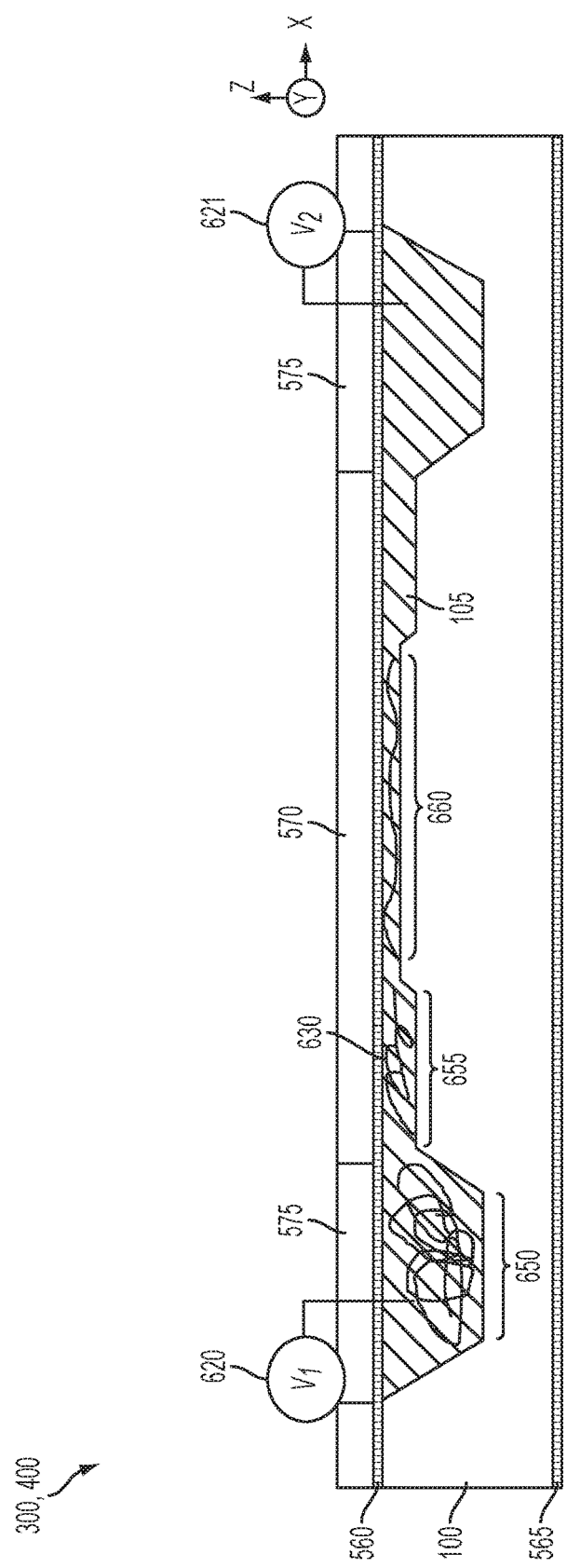
FIG. 6 is a schematic illustrating biopolymer movement of the biopolymers in the fabricated channel device according to an embodiment.

FIG. 6 is a schematic illustrating biopolymer movement of the biopolymers 630 in the fabricated channel device (300, 400) in any FIGS. 1-5 according to embodiments. The biopolymer 630 may be DNA, RNA, proteins, etc. Voltage sources 620 and 621 generate an electric field that drives the biopolymer 630 to flow from microchannel regions (e.g., wider widths and corresponding deeper depths) to nanochannel regions (e.g., smaller widths and corresponding smaller depths) and gradually stretches the biopolymers 630 as they flow.

The gradually reduced channel dimensions force the biopolymers 630 to decoil as it travels through the channel 105. Therefore, the chance of channel clogging is greatly reduced and the rate of translocating the biopolymers 630 is greatly enhanced. For example, the biopolymer 630 is in a coiled state 650 in the largest width and largest depth of the channel 105. After traversing (from the previous larger width and depth region) to a smaller width and depth region of the channel 105, the biopolymer 630 is forced into a less coiled state 655. After traversing (from the previous larger region) to the smallest width and depth region of the channel 105, the biopolymer 630 is forced into an uncoiled (straightened) state 660. FIG. 6 only shows the biopolymer 630 moving between three regions with three states 650, 655, 660. It is contemplated that the biopolymer 630 may move between seven channel regions in FIG. 3 and/or the eight channel regions in FIG. 4, which continuously uncoil the biopolymer 630 as it travels into more and more confined spaces (i.e., according to the depth and width gradient).

Figure 7B:
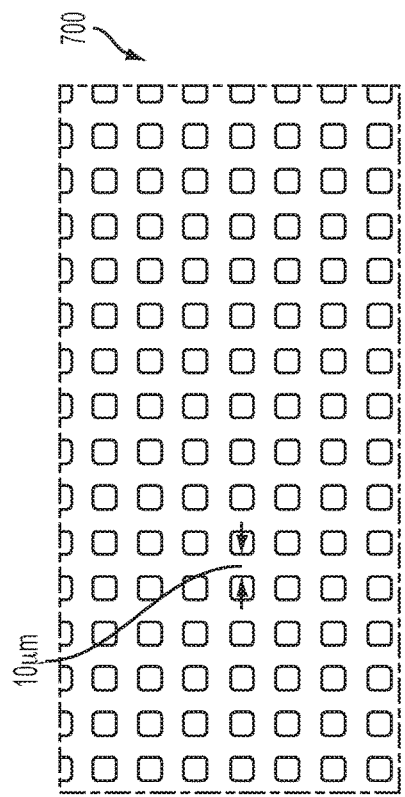
FIGS. 7A, 7B, and 7C illustrate an example of a sealed channel device (i.e., sealed chip) according to an embodiment.
Figure 7C:
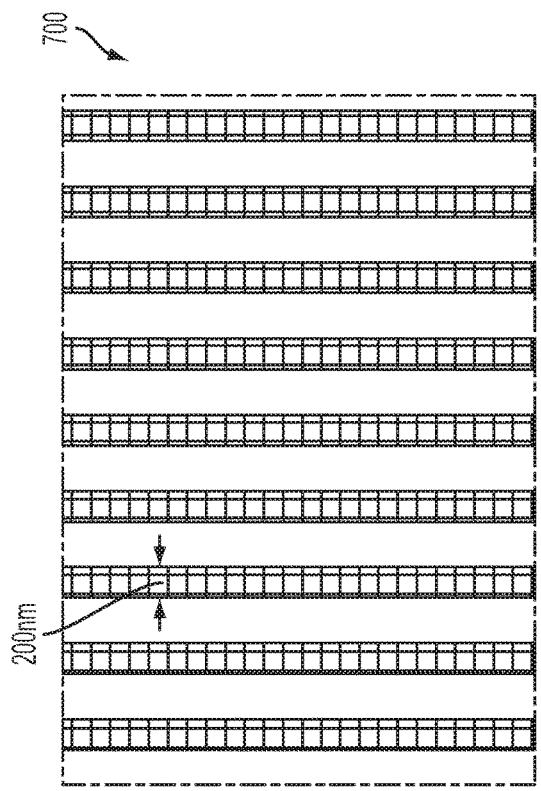
Figure 7A:
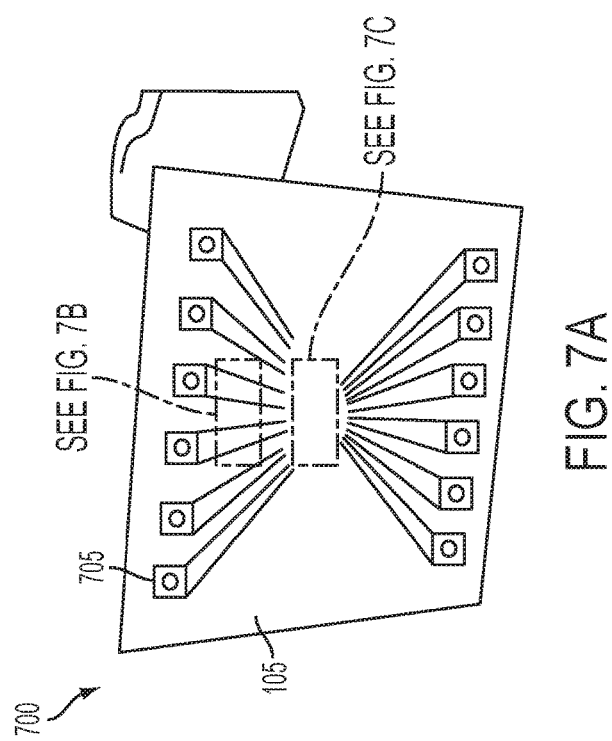

FIGS. 7A, 7B, and 7C (generally referred to as FIG. 7) are an example of a sealed channel device 700 (i.e., sealed chip) according to an embodiment. The sealed channel device 700 may incorporate nanodevices and features discussed in FIGS. 1-6. FIG. 7 shows an example of patterning the channels 105 (i.e., fluidic channels) with microchannel features and nanochannel features.

FIG. 7A is an optical microscope image of the sealed channel device 700 (sealed biochip). FIG. 7A shows the reservoirs 705 in which the biopolymers 630 are deposited.

FIG. 7B is an enlarged view of one section in FIG. 7A. In FIG. 7B, the enlarged view is an optical image of one microchannel region to show the 10 μm channel dimension in the channel 105. There are larger and smaller microchannel regions as discussed herein.

FIG. 7C is an enlarged view of another section in FIG. 7A. In FIG. 7C, the enlarged view is an electron microscope image of nanochannels to show 200 nm wide channels in the channel 105. There are larger and smaller nanochannel regions as discussed herein.

Figure 8B:
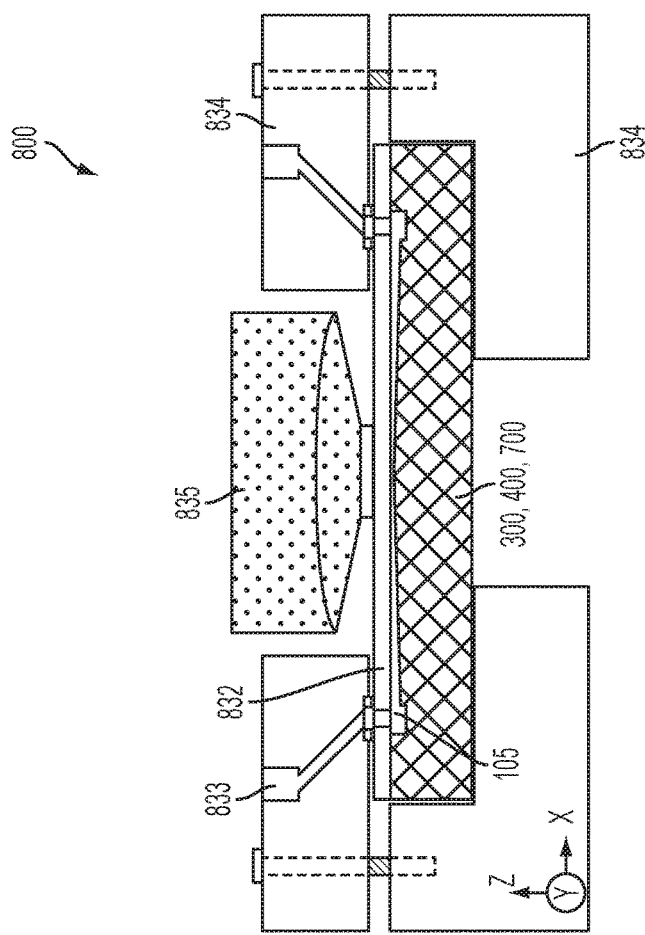
FIGS. 8A and 8B illustrate an example of a fluidic system according to an embodiment.
Figure 8A:
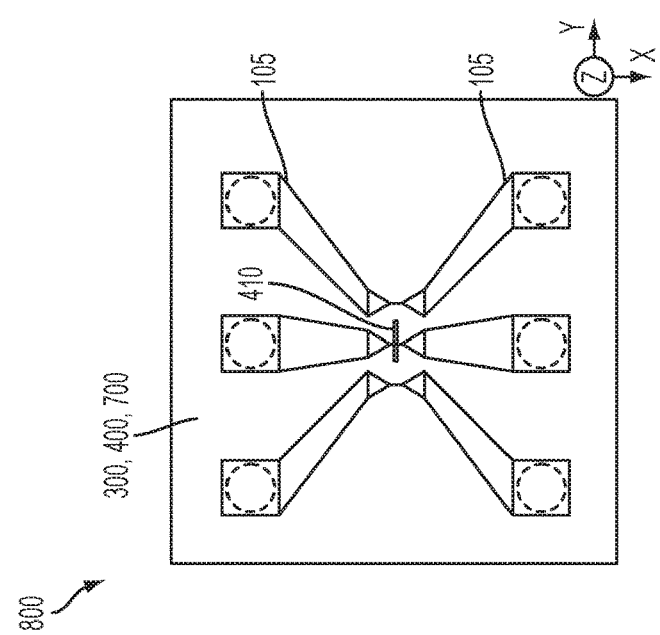

FIGS. 8A and 8B (generally referred to as FIG. 8) illustrate an example of a fluidic system 800 according to an embodiment. FIG. 8 shows an example use of the fabricated channel devices (discussed in FIGS. 1-7) for sensing.

FIG. 8A is a top-view schematic of the chip 300, 400, 700 to illustrate example integration of electronic sensors, i.e., such as the electronic detector 410.

FIG. 8B is a cross-sectional view of an optical imaging setup for the fluidic system 800. FIG. 8B shows that the chip 300, 400, 700 is sealed, mounted to a fluidic jig 834, and brought to a fluorescence microscope 835 for optical and fluorescence imaging. For example, the fluidic chip 300, 400, 700 may be sealed with a sealing layer 832, which may be an insulating dielectric layer. The sealed fluidic chip is mounted on the fluidic jig 834 and aligned to external fluidic reservoirs 833 for fluidic and biopolymer manipulation. The fluorescence microscope is mounted to image the biopolymer 630 flowing in the chip 300, 400, 700.

An electrolyte solution fills the channels and reservoirs. The electrolyte solution is a conductive fluid, such as a salt solution with ions for conducting electricity when a voltage is applied.

Figure 9:
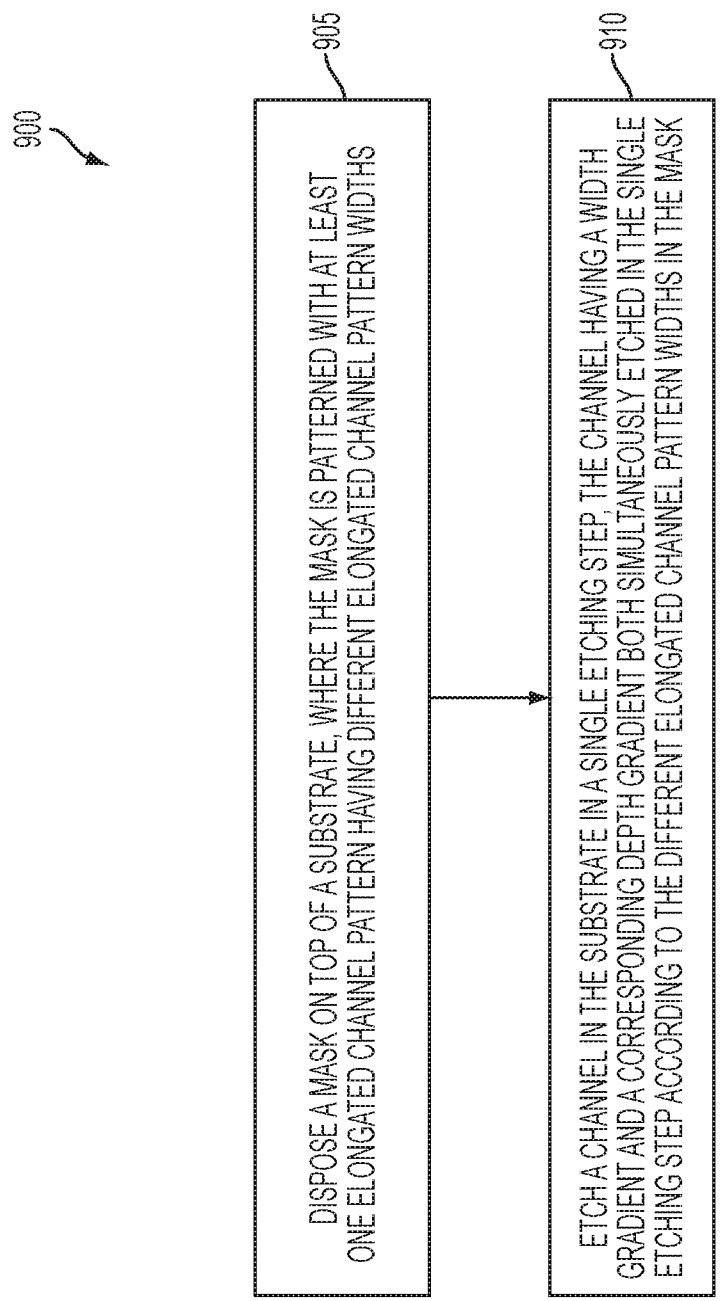
FIG. 9 is a method of forming gradient channels with width and depth gradients according to embodiment.

FIG. 9 is a method 900 of forming gradient channels 105 with width and depth gradients according to embodiment. Reference can be made to FIGS. 1-8 and 10.

At block 905, the mask 350 is disposed on top of the substrate 101, where the mask is patterned with elongated channel patterns (example the channel patterns in mask 350 are shown in FIGS. 3, 4, and 5) having different elongated channel pattern widths.

At block 910, the channels 105 are etched in the substrate 101 in a single etching step, such that the channels 105 have a width gradient and a corresponding depth gradient both simultaneously etched in the single etching step according to the different elongated channel pattern widths in the mask 350.

The width gradient has a first width (w1) through a last width (wn) that corresponds on a one-to-one basis to a first vertical depth (d1) through a last vertical depth (dn) of the depth gradient. The first width (w1) is the smallest width and the last width (wn) is the widest width. The first depth is the shallowest depth and the last depth is the deepest depth.

The method includes limiting depths of the depth gradient according to the respective widths of the width gradient during the single etching step such that the depths of the depth gradient maintain a preset/predefined relationship to the respective widths of the channel 105.

The depth gradient etched in the single etching step has channel depths changing in different regions 305, 310, 315, 320, 325, 330, 335, 405 of the channel 105 according to a respective width in those different regions. The depth gradient from the first depth through the last depth changes from less than 10 nanometers in the smallest width region to several micrometers in the largest width region.

The single etching step is anisotropic etching of the substrate through openings of the elongated channel pattern (in the mask 350) having the different elongated channel pattern widths in the mask.

The depth gradient of the channels 105 reduces an entropic barrier of biopolymers 630 traversing through the channels 105 as discussed in FIG. 6.

Multiple channels 105 (e.g., and array of channels) with different widths and corresponding different depths are simultaneously etched during the single etching step.

The depth gradient of the channels 105 includes a nanochannel region having a nanochannel depth ranging from less than 10 nanometers to a few hundred nanometers. The nanochannel depth is determined by lateral dimensions (respective widths) of the channel 105 in the nanochannel region and fixed during over etching. Over etching during the single etching step does not increase the nanochannel depth. During the single etching step, over etching is prolonging a wet etching time T beyond requirements to etch the nanochannel depth all while the nanochannel depth does not increase beyond a predetermined maximum nanochannel depth set by a nanochannel width. The depth gradient of the channel 105 includes a microchannel region having a microchannel depth that is controlled by the wet etching time T during the single etching step. When over etching with the wet etching time beyond requirements to etch the microchannel depth during the single etching step, the microchannel depth does not significantly increase beyond a predetermined maximum microchannel depth set by a microchannel width. The microchannel width of the microchannel region is wider than the nanochannel width of the nanochannel region.

The method includes shrinking a width and a depth of the channel by oxidation (e.g., oxidation layer 560 and 565) of the substrate 101 such that a smallest width and a shallowest depth of the channel 105 are each less than 5 nanometers.

The material of the substrate 101 includes at least one of Si, Ge, GaAs, and sapphire. Wet etching during the single etching step is configured to process tens or hundreds of wafers in a single batch, which is different from dry etching which processes one wafer at a time.

The single etching step is a single continuous wet etching event of removing material of the substrate 101 at different depths according to each different elongated channel pattern width in the mask 350 for the different elongated channel pattern widths. The single etching step forms the channels 105 with the different depths based on different widths of the channels 105 without requiring a separate etching step to etch the different depths. The mask 350 is removed from the substrate 101.

Figure 10A:
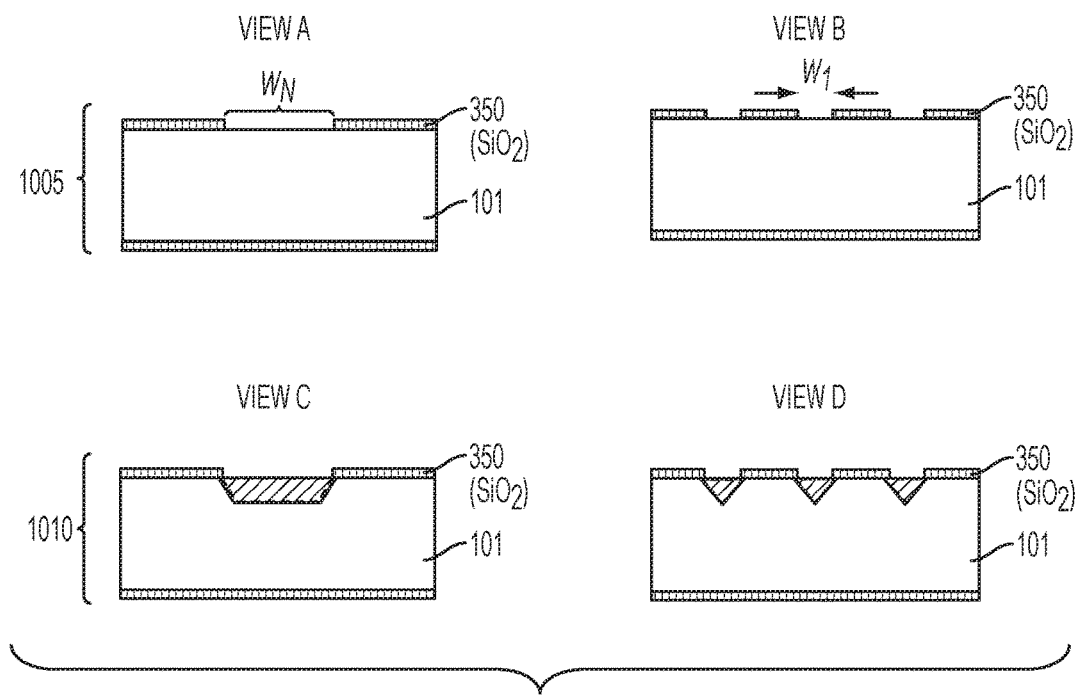
FIGS. 10A and 10B illustrate an etching scenario that provide additional explanation according to embodiments discussed herein.
Figure 10B:
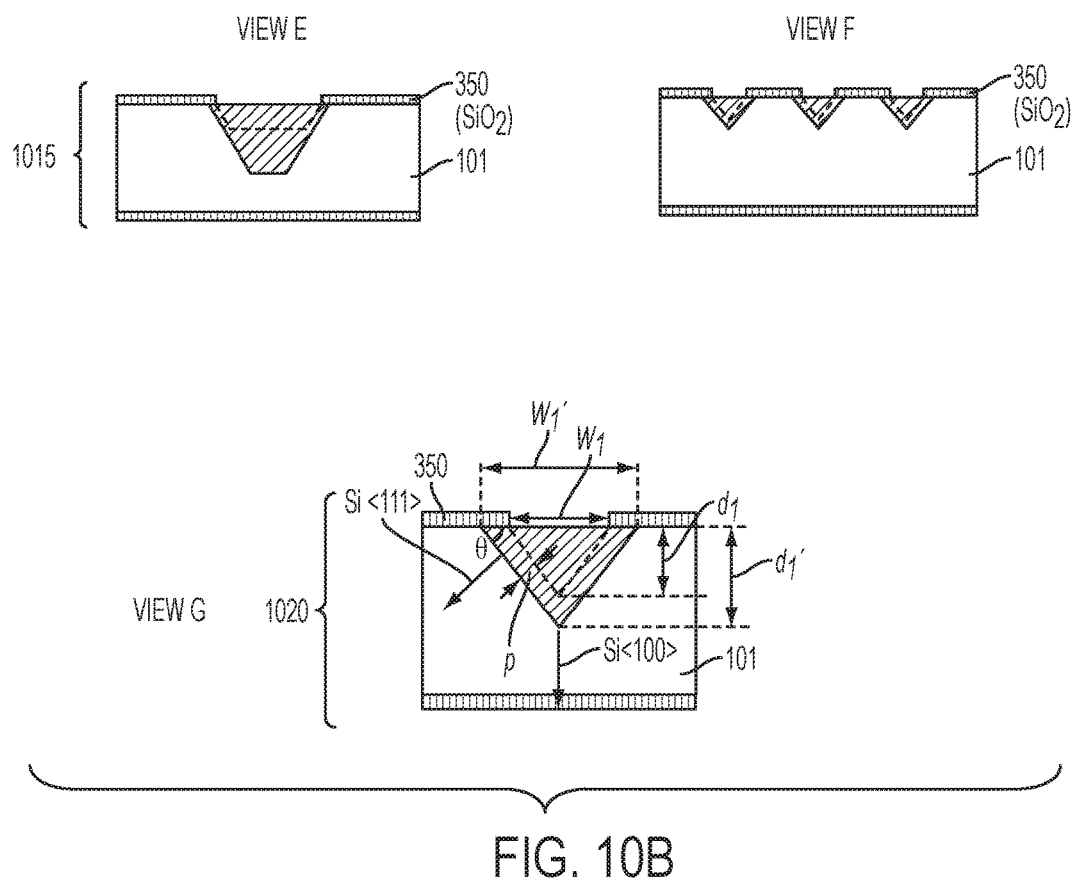

Now turning to FIGS. 10A and 10B, an etching scenario is discussed to provide further explanation according to embodiments discussed herein. Consider an etching rate of Si (100) plane as $R_{100}$, and an etching rate of Si (111) plane as $R_{111}$. The etching rate ratio $\varepsilon = R_{100}/R_{111}$ is ideally infinitely large, but in reality it is a finite large number (e.g. 10-500), depending on many etching parameters. Such a finite etching of the Si (111) plane may cause a slight undercut and widen the formed nanochannel. FIGS. 10A and 10B show how to determine the nanochannel depth and width with a given etching rate. Also, FIGS. 10A and 10B illustrate the calculation of Si nanochannel width and depth with the Si (111) plane being etched.

At block 1005, the SiO$_2$ mask is patterned on Si before etching (i.e., at time T=0). View A shows a microchannel region with a mask pattern width $W_N$, and view B shows nanochannel region with a mask pattern width $W_1$.

At block 1010, the channels are etched for a time T=$t_0$ so that the microchannel region has a flat bottom in view C and the nanochannel region has the sharp triangular bottom in view D.

At block 1015, channels are etched for a time T=$t_1$ so that the microchannel has been etched to reach the target depth (which can be a triangular bottom when the microchannel region is to reach its maximum depth) in view E. View F shows that the nanochannel region has a vertical depth that remains unchanged even though the etching time has increased to from time $t_0$ to $t_1$. Note that time T=$t_0$ is greater than time T=0, and time T=$t_1$ is greater than time T=$t_0$.

Block 1020 shows detailed geometry of the channel region (which can represent the nanochannel region and/or microchannel region.

Now, a practical application is provided to discuss how to control the channel geometry with finite etching selectivity ε. In this example, it is assumed that $R_{100}$=10 nm/sec, $R_{100}$=0.2 nm/sec, and ε=50.

(1) As an exemplary number for the estimation, it is assumed that the microchannel width $W_N$=5 μm and nanochannel width $W_1$=100 nm.

(2) From the nanochannel geometry, at about $$T = t_0 = \frac{0.41 w_N}{R_{100}} \left( \frac{\varepsilon}{0.58\varepsilon - 1} \right) = 7.3 \sec,$$

the nanochannel region has the sharp triangular bottom formed. At this time, the microchannel depth and nanochannel depth are both 73 nanometers. After this time point, the microchannel depth is continuously increased as the Si (100) plane is consumed, but the nanochannel depth is almost fixed but increases slowly due to the etching of exposed Si (111) plane.

(3) Assume we control the final etching time to form 500 nm deep microchannels. The time required is thus 50 sec. The overetch time for nanochannel region is thus 43 sec (which is approximately 600% overetch). Due to etching of Si (111) plane, with a dimension $w_1$ in the SiO$_2$ mask, the final etched channel has a lateral dimension of $w_1$' slightly larger than $w_1$, and the depth $d_1$' is slightly larger than the ideal depth $d_1$. From the structural geometry as shown in view G of FIG. 10B, we get $d_1$'=$w_1$'×η, $d_1$=$w_1$×η, where η=0.5×tan 54.7°=0.707. It is noted that η=tan θ

Here, we assume "p" is the etched depth of Si (111) during the 50 s etch, and can be found as 50*0.2=100 nm. Therefore, the final nanochannel width $w_1$' and depth $d_1$' can be calculated from the lateral undercut "p" as 124 nm and 88 nm (respectively), which is only 24 nm and 15 nm larger than ideal width $w_1$ and depth $d_1$. At the same time, the microchannel depth is 500 nm, much greater than the depth of the nanochannel.

The most effective (but not necessary) way to minimize the undercut ("p") is to minimize the Si (111) etching, or to increase the etching selectivity $\varepsilon = R_{100}/R_{111}$. For example, if we increase ε to 100 instead of 50, the width $w_1$' and depth $d_1$' are changed to 112 nm and 79 nm, respectively. On the other hand, the undercut ("p") from Si (111) etching enlarges the channel dimensions, and it does so uniformly for all nanochannels. This means an oxidation or conformal deposition step can uniformly reduce the channel dimensions after etching and restore the desired widths and depths for all nanochannels.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method of forming a gradient channel with width and depth gradients, the method comprising:
   disposing a mask on top of a substrate, wherein the mask is patterned with at least one elongated channel pattern having different elongated channel pattern widths; and
   etching a channel in the substrate in a single etching step, the channel having a width gradient and a depth gradient both simultaneously etched in material of the substrate in the single etching step according to the different elongated channel pattern widths in the mask;
   wherein the depth gradient of the channel includes a nanochannel region having a nanochannel depth ranging from less than 10 nanometers to a few hundred nanometers caused by etching the channel in the material of the substrate during the single etching step;
   wherein the nanochannel region having the nanochannel depth comprises a triangular shaped bottom while a microchannel region having a microchannel depth comprises a flat bottom;
   wherein the nanochannel depth is determined by lateral dimensions of the channel in the nanochannel region and is fixed during over etching;
   wherein, during the single etching step, over etching is prolonging a wet etching time beyond requirements to etch the nanochannel depth all while the nanochannel depth does not increase beyond a predetermined maximum nanochannel depth set by a nanochannel width.

2. The method of claim 1, wherein the width gradient has a first width through a last width that corresponds on a one-to-one basis to a first depth through a last depth of the depth gradient.

3. The method of claim 2, wherein the first width is a smallest width and the last width is a widest width; and
   wherein the first depth is a shallowest depth and the last depth is a deepest depth.

4. The method of claim 1, further comprising limiting depths of the depth gradient according to respective widths of the width gradient during the single etching step such that the depths of the depth gradient maintain a preset relationship to the respective widths of the channel.

5. The method of claim 2, wherein the depth gradient etched in the single etching step has channel depths changing in different regions of the channel according to a respective width in the different regions.

6. The method of claim 2, wherein the depth gradient from the first depth through the last depth changes from less than 10 nanometers to several micrometers.

7. The method of claim 1, wherein the single etching step is anisotropic etching of the substrate through openings of the at least one elongated channel pattern having the different elongated channel pattern widths in the mask;
   wherein the depth gradient of the channel reduces an entropic barrier of biopolymers traversing through the channel;
   wherein multiple channels with different widths and corresponding different depths are simultaneously etched during the single etching step.

8. The method of claim 1,
   wherein over etching during the single etching step does not increase the nanochannel depth.

9. The method of claim 8, wherein the depth gradient of the channel includes a microchannel region having a microchannel depth that is controlled by the wet etching time during the single etching step.

10. The method of claim 9, wherein, when over etching with the wet etching time beyond requirements to etch the microchannel depth during the single etching step, the microchannel depth does not increase beyond a predetermined maximum microchannel depth set by a microchannel width.

11. The method of claim 10, wherein the microchannel width of the microchannel region is wider than the nanochannel width of the nanochannel region.

12. The method of claim 1, further comprising shrinking a width and the nanochannel depth of the channel by oxidation of the substrate such that a smallest width and a shallowest depth of the channel is less than 5 nanometers.

13. The method of claim 1, wherein material of the substrate includes at least one of Si, Ge, GaAs, and sapphire.

14. The method of claim 1, wherein wet etching during the single etching step is configured to process tens or hundreds of wafers in a single batch, which is different from dry etching which processes one wafer at a time.

15. The method of claim 1, wherein the single etching step is a single continuous wet etching event of removing material of the substrate at different depths according to each different elongated channel pattern width in the mask for the different elongated channel pattern widths;
   wherein the single etching step forms the channel with the different depths based on different widths of the channel without requiring a separate etching step to etch the different depths; and
   wherein the mask is removed from the substrate.

16. A method of forming a gradient channel with width and depth gradients, the method comprising:

applying a mask on top of a substrate, wherein the mask is patterned with at least one elongated channel pattern having different elongated channel pattern widths; and etching a channel in the substrate in a single etching step, the channel having a width gradient and a depth gradient both simultaneously etched in material of the substrate in the single etching step according to the different elongated channel pattern widths in the mask;

wherein the depth gradient of the channel includes a nanochannel region having a nanochannel depth caused by etching the channel in the material of the substrate during the single etching step;

wherein the nanochannel depth is determined by lateral dimensions of the channel in the nanochannel region and is fixed during over etching;

wherein the nanochannel region having the nanochannel depth comprises a triangular shaped bottom while a microchannel region having a microchannel depth comprises a flat bottom;

wherein, during the single etching step, over etching is prolonging a wet etching time beyond requirements to etch the nanochannel depth all while the nanochannel depth does not increase beyond a predetermined maximum nanochannel depth set by a nanochannel width.

17. The method of claim 16, wherein over etching during the single etching step does not increase the nanochannel depth.

18. A method of forming gradient channels with width and depth gradients, the method comprising:

disposing a mask on top of a substrate, wherein the mask is patterned with an array of elongated channel patterns having different elongated channel pattern widths; and etching an array of channels in the substrate in a single etching step, the array of channels each having a width gradient and a depth gradient both simultaneously etched in material of the substrate in the single etching step according to the different elongated channel pattern widths in the mask;

wherein the depth gradient of the array of channels includes a nanochannel region having a nanochannel depth caused by etching the channel in the material of the substrate during the single etching step;

wherein the nanochannel depth is determined by lateral dimensions of respective channels in the nanochannel region and is fixed during over etching;

wherein the nanochannel region having the nanochannel depth comprises a triangular shaped bottom while a microchannel region having a microchannel depth comprises a flat bottom;

wherein, during the single etching step, over etching is prolonging a wet etching time beyond requirements to etch the nanochannel depth all while the nanochannel depth does not increase beyond a predetermined maximum nanochannel depth set by a nanochannel width.

19. The method of claim 18, wherein the width gradient has a first width through a last width that corresponds on a one-to-one basis to a first depth through a last depth of the depth gradient.

20. The method of claim 19, wherein the first width is a smallest width and the last width is a widest width; and wherein the first depth is a shallowest depth and the last depth is a deepest depth.

* * * * *